United States Patent [19]

Nakamura et al.

[11] 4,321,123
[45] Mar. 23, 1982

[54] COENZYME IMMOBILIZED ELECTRODE

[75] Inventors: Kenichi Nakamura, Hirakata; Shiro Nankai, Neyagawa; Takashi Iijima, Kirakata, all of Japan

[73] Assignee: Matsushita Electric Industrial Co., Ltd., Osaka, Japan

[21] Appl. No.: 194,271

[22] Filed: Oct. 6, 1980

Related U.S. Application Data

[63] Continuation of Ser. No. 32,929, Apr. 19, 1979, abandoned.

[30] Foreign Application Priority Data

Apr. 21, 1978 [JP] Japan .................................. 53/47984
Apr. 21, 1978 [JP] Japan .................................. 53/47985

[51] Int. Cl.³ .......................................... C12Q 11/00
[52] U.S. Cl. .................................. 204/195 B; 435/4; 435/288; 435/817
[58] Field of Search ............... 204/195 B, 1 E, 195 P, 204/195 R; 435/4, 288, 817

[56] References Cited

U.S. PATENT DOCUMENTS 3,539,455 11/1970 Clark .................................. 204/1 T
4,100,029 7/1978 Prosperi et al. ......... 195/DIG. 11 X
4,151,049 4/1979 Janata ................................. 204/1 T

FOREIGN PATENT DOCUMENTS 1959169 6/1970 Fed. Rep. of Germany .

OTHER PUBLICATIONS

W. J. Blaedel et al., Anal. Chem., v. 48, No. 8, pp. 1240–1247, (1976).
F. R. Shu et al., Anal. Chem., vol. 48, p. 1679, (1976).
R. A. Kamin et al., ACS Symp. Ser., 38, p. 170, (1977).

Primary Examiner—G. L. Kaplan
Attorney, Agent, or Firm—Wenderoth, Lind & Ponack

[57] ABSTRACT

Improvements in a coenzyme electrode used to electrochemically measure the activity of enzyme or substrate concentration of the enzyme easily. The coenzyme is immobilized, without using a semipermeable membrane, on the electron collector directly with the chemical bond, particularly the covalent bond, whereby the activity of the oxido-reductase requiring the coenzyme can be measured. In addition, the oxido-reductase requiring the coenzyme is also immobilized together with such immobilized coenzyme to improve the characteristics of the conventional enzyme-coenzyme immobilized electrode.

5 Claims, 12 Drawing Figures

COENZYME IMMOBILIZED ELECTRODE

This is a continuation of application Ser. No. 32,929, filed Apr. 19, 1979 and now abandoned.

The present invention relates to improvements in coenzyme electrodes to be used to electrochemically and easily measure the substrate concentration of the enzyme. Also, the present invention relates to electrodes for quickly measuring the activity of the enzyme.

The conventional example of the enzyme electrode composed of immobilized oxidoreductase and coenzyme is described in literature (Anal. Chem. 48(8), 1240, 1976). This is a sensor for lactic acid using lactate dehydrogenase (LDH) as the oxidoreductase, nicotineamide adenine dinucleotide (NAD) as the coenzyme, and carbon as electron collector. As shown in FIG. 1, according to this principle, the lactic acid (AH2) as the substrate is dehydrogenated (oxidized) by the enzyme catalytic reaction, and a hydrogen atom (electron) moves to NAD (oxidized) to produce anodic current when the resultant NADH (reduced NAD) is directly oxidized on the electron collector. Since the oxidation current value of the NADH varies in accordance with the concentration of the lactic acid as the substrate, the substrate concentration can be obtained from the measurement of the anodic current.

In the above-described literature, the following two types of constructions are shown as the electrode with the enzyme and coenzyme being immobilized.

(1) As shown in FIG. 2, an electrode wherein the LDH 1 and NAD 2 are crosslinked on semipermeable membrane 5 with glutaraldehyde, and the enzyme and coenzyme immobilized on the surface of the membrane are physically brought into contact against the carbon electron collector 3.

(2) As shown in FIG. 3, an electrode wherein agarose, which is one type of polysaccharide, is used as polymer carrier 6, the NAD is immobilized on the carrier, and the macro-molecular NAD is adapted to be retained, together with the enzyme, in the space between the carbon electron collector 3 and the semipermeable membrane covering the carbon electron collector. In this case, the enzyme is not chemically modified particularly. In FIG. 3, reference numberal 4 represents a covalent bond.

Both of the above described enzyme electrodes (1) and (2) have the following problems.

(a) In the case of measuring the activity of an enzyme, the enzyme itself cannot be diffused into the semipermeable membrane because the surface of the electron collector is covered with the semipermeable membrane. Thus, the activity of the enzyme cannot be measured by the electrode with only the coenzyme, except for the enzyme, being immobilized.

(b) In the case of measuring the lactic acid concentration, it takes time for the lactic acid as the substrate to pass the semipermeable membrane for diffusion thereinto and to come into contact against the enzyme. Thus, it takes time from injection of a lactic acid containing liquid as a specimen to be measured, to provision of the measured value (more than ten minutes), and the response current value to be obtained is small.

(c) The response current value to be obtained is small. Accordingly, the analytical sensitivity is lower.

The present invention is created to solve the problems of the above-described enzyme electrode and, according to the present invention, there is provided a coenzyme immobilized electrode comprising a coenzyme of oxidoreductase, and an electron collector, said coenzyme being supported through covalent bonding on said electron collector or on a carrier which is mixed with said electron collector.

The coenzyme immobilized electrode of the present invention is characterized in that the coenzyme is immobilized, without using the semipermeable membrane, on the electron collector directly, or on the carrier which is mixed with the electron collector, whereby the activity of the oxidoreductase requiring the coenzyme can be measured. In addition, the oxidoreductase requiring the coenzyme is also immobilized together with such immobilized coenzyme as described hereinabove to improve the characteristics of the conventional enzyme-coenzyme immobilized electrode.

These objects and advantages will be more readily apparent from the detailed description in conjunction with the preferred embodiments and the following drawings in which.

The present invention will be described hereinafter with reference to the embodiments.

EMBODIMENT 1

$SnO_2$ nesa-glass (semiconductive $SnO_2$ thin membrane attached on glass plate) is used as the electron collector, the LDH as the enzyme, and the NAD as the coenzyme.

As shown in the following equation, the NAD reacts with succinic anhydride in dimethyl sulfoxide (DMSO) and a carboxyl group is introduced into the molecule.

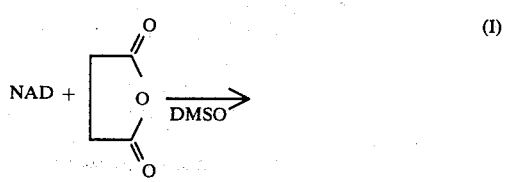
(I)

-continued

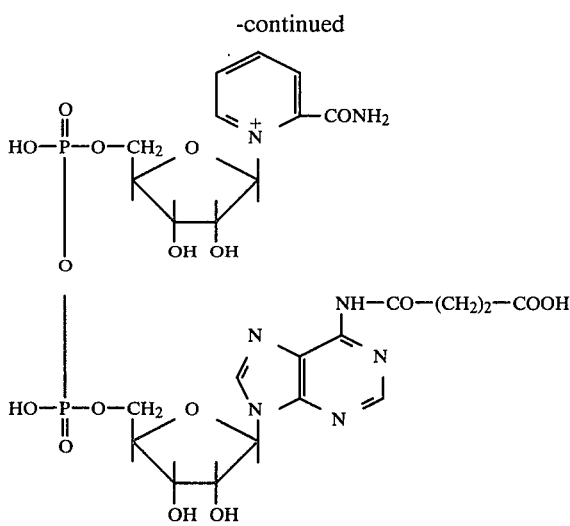

The NAD derivative (I) reacts with the hydroxyl group on the SnO$_2$ surface in the presence of dicyclohexyl carbodiimide (DCC) to produce an ester bond, thereby to immobilize the NAD on the SnO$_2$ nesa-glass surface.

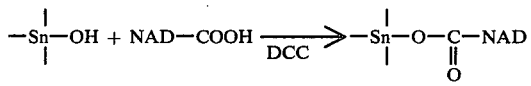

Figure 4:
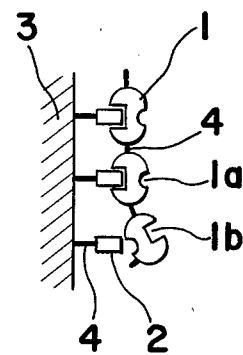
FIG. 4, FIG. 10, FIG. 11 and FIG. 12 are respectively the typical views each showing the construction of the coenzyme-enzyme immobilized electrode of the present invention.

The NAD immobilized SnO$_2$ nesa-glass electrode produced in the above-described manner is dipped in a solution containing the LDH to produce a complex of the NAD and the LDH. It is treated with a cross-linking reagent such as glutaraldehyde or the like to further immobilize the LDH on the electron collector. In this case, the LDH forms the complex thereof with the NAD and are bonded, with each other, with the cross-linking reagent, and is immobilized on the electron collector. The construction of the NAD-LDH immobilized electrode produced is shown in FIG. 4, wherein there are an enzyme 1 having a substrate bonding site 1a and the coenzyme bonding site 1b, a coenzyme 2, an electron collector 3 and covalent bond 4.

Figure 5:
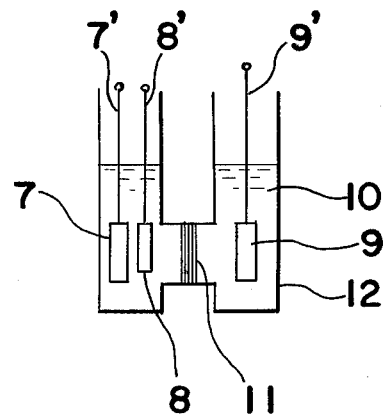
FIG. 5 is a schematic view of a measuring system to be employed for the electrode of the present invention.

FIG. 5 shows a measuring system wherein the above-described coenzyme immobilized electrode or the coenzyme-enzyme immobilized electrode are incorporated. Referring to FIG. 5, there are shown the above-described two types of electrodes 7 with the lead wire 7' thereof, a saturated calomel electrode 8 for a reference electrode with the lead wire 8' thereof, a counter electrode 9 with the lead wire 9' thereof, a buffer solution 10, a separator 11, and an electrolytic cell 12.

A case where the above-described coenzyme electrode is used as the electrode 7 to measure the enzyme activity will be described hereinafter. The electrode 7 is set to a constant-potential of 0.4 V with respect to the electrode 8, using a potentionstat. Add the LDH into the buffer solution containing 0.1 mol per l lactate, and the anodic current flowing between the electrode 7 and the counter-electrode 9 increases.

Figure 6:
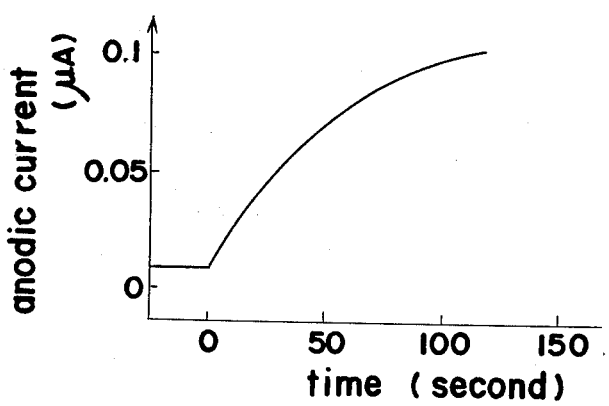
FIG. 6 is a graph showing the anodic current response of the NAD immobilized electrode through addition of LDH in accordance with the present invention.
Figure 7:
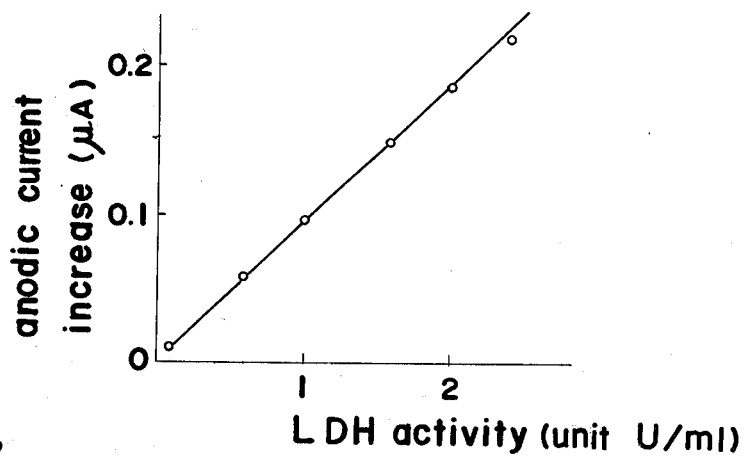
FIG. 7 shows the relationship between the LDH activity and the anodic current increase.

FIG. 6 shows the anodic current response when the LDH has been added into the buffer solution so that the LDH activity in the buffer solution may become 1 U/ml. The current shows a steady state value in approximately two minutes after the addition of the LDH, and indicates the current increase of 0.1 μA. FIG. 7 shows the relationship between the LDH activity and the current increase amount. Thus, the linear relationship is recognized between the current values in the range of 0.1 to 2 U/ml in LDH activity. It is found that it is possible to measure the LDH activity by the coenzyme immobilized electrode.

A case where the coenzyme-enzyme immobilized electrode is used as the electrode 7 to measure the substrate concentration will be described hereinafter. The electrode 7 is set to a constant-potential of 0.4 V with respect to the electrode 8, using a potentionstat. Add the lactic acid into the buffer solution and the anodic current flowing between the electrode 7 and the counter electrode 9 increases.

Figure 8:
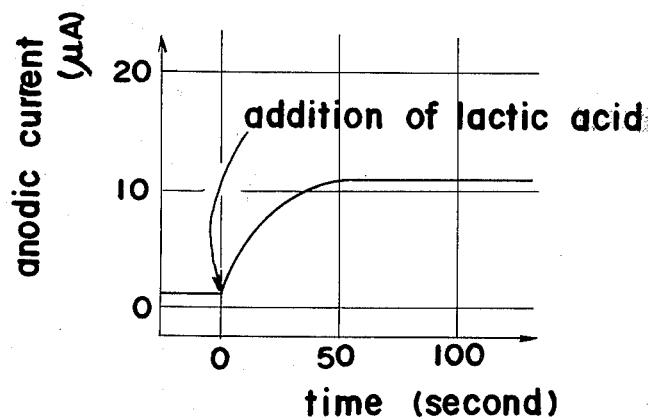
FIG. 8 shows the anodic current of the NAD-LDH immobilized electrode through addition of lactic acid.

FIG. 8 shows the anodic current response when the lactic acid has been added so that the lactic acid concentration in the buffer solution may become $10^{-3}$ mol per l. The current shows a steady state value in approximately one minute and the current increase of 10 μA is recognized.

Figure 9:
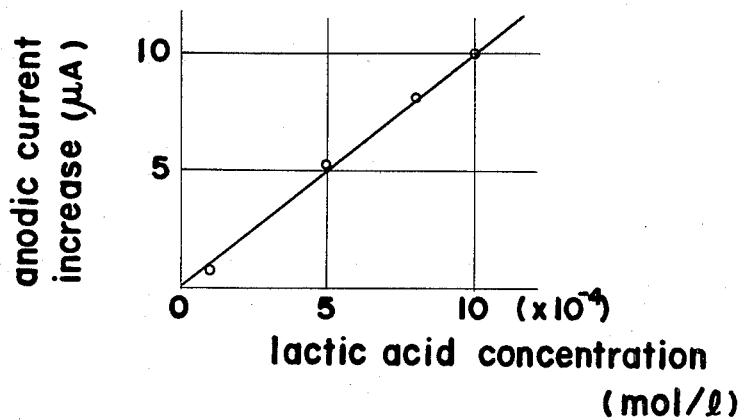
FIG. 9 shows the relationship between the lactic acid concentration and anodic current increase.

FIG. 9 shows the relationship between the lactic acid concentration and the current increase amount. Thus, the linear relationship between the concentration and the current value is recognized in the range of $10^{-4}$ to $10^{-3}$ mol per l in lactic acid concentration. It is found that the estimation of the lactic acid can be made by the electrode used herein.

EMBODIMENT 2

SnO$_2$ nesa-glass is used as the electron collector and carrier, glutamate dehydrogenase (GDH) as the enzyme and NAD as the coenzyme.

The surfaces of the nesa-glass are chemically modified in the procedure shown in the following equation.

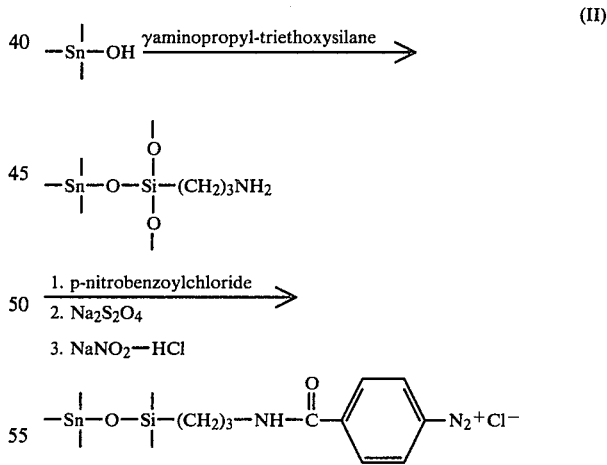

(II)

Figure 10:
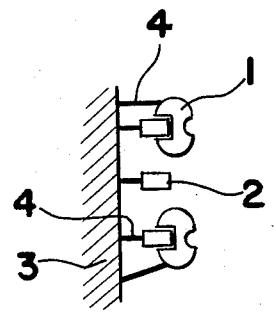

NAD alone is, or NAD and GDH are simultaneously, diazocoupled with respect to the nesa-glass derivative (II), thus providing an electrode wherein the coenzyme alone or the coenzyme and enzyme are immobilized on the nesa-glass through covalent bonding. FIG. 10 shows a typical scheme of the coenzyme-enzyme immobilized electrode.

Measurement of the GDH activity of 0.1 to 1.3 U/ml could be made, in the same manner as in the embodiment 1, by the NAD immobilized electrode thus made. Also, according to the similar measurement as the embodiment 1 using the NAD-GDH immobilized electrode, the current increase of approximately 15 μA was recognized with respect to the glutamic acid concentration of $1\times 10^{-3}$ mol per l. The current reached the steady state value in 0.5 minute after the addition of the glutamic acid. And the estimation of the glutamic acid could be made in the concentration range of $1\times 10^{-4}$ to $3\times 10^{-3}$ mol per l.

EMBODIMENT 3

Graphite is used as the electron collector, isocitrate dehydrogenase (ICDH) as the enzyme, and nicotine amide adenine dinucleotide phosphate (NADP) as the coenzyme. The graphite powder surfaces are nitrated and furthermore are reduced.

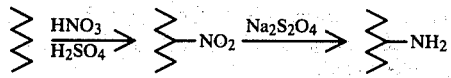

On the other hand, the carboxyl group is introduced into the NADP in the same manner as in the embodiment 1. Furthermore, the NADP derivative reacts with the graphite derivative under the existence of DCC and is immobilized on the graphite surface by the amide bond.

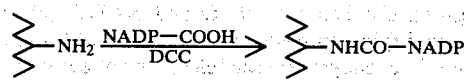

The NADP immobilized graphite powders are press-molded into plate shape to make the NADP immobilized electrode. In addition, the electrode is dipped in a solution containing ICDH and thereafter is dried and the glutaraldehyde is added thereby to further immobilize enzyme on the graphite electron collector.

In the same manner as in the embodiment 1, the ICDH activity of 0.1 to 0.6 U/ml could be measured by the NADP immobilized electrode made as described hereinabove. Also, the coenzyme-enzyme immobilized electrode showed an increase of current of approximately 2.5 μA with respect to the concentration increase of isocitric acid of $1\times 10^{-3}$ mol per l and reached the steady state current after one minute. And the estimation of the isocitric acid could be made in the concentration range of $1\times 10^{-4}$ to $1\times 10^{-3}$ mol per l.

EMBODIMENT 4

The NAD was used as the coenzyme, albumin as the carrier and graphite as the electron collector.

After the NAD and albumin have been mixed with a small quantity of water, glutaraldehyde is added to the mixture and the NAD can be immobilized on the albumin surface. The reaction is considered to occur through the cross-linking of the amino group of the NAD and SH groups of albumin by the glutaraldehyde.

The NAD immobilized albumin powders made as described hereinabove are mixed with the graphite powders and are press-molded to make the coenzyme immobilized electrode.

Figure 11:
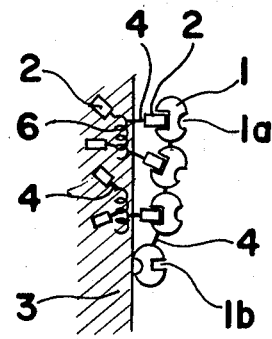

In addition, the NAD immobilized electrode is dipped in a solution containing GDH. After the complex of the NAD and the enzyme has been formed, the glutaraldehyde is further added to cross-link the enzyme. FIG. 11 shows the construction of the NAD-GDH immobilized electrode where the carrier albumin is 6. The same measurement, as in the embodiment 1, by use of the above-described coenzyme immobilized electrode, showed that the linear relationship was obtained between the current values in the range of 0.1 to 1.5 U/ml.

Also, the same measurement as in the embodiment 1 by the above-described NAD-GDH immobilized electrode showed that the current increase of approximately 6 μA was obtained with respect to the increase in the concentration of the glutamic acid of $1\times 10^{-3}$ mol per l and the current reached the steady state value after one minute. And the estimation of the glutamic acid in the concentration range of $2\times 10^{-4}$ to $3\times 10^{-3}$ mol per l could be made.

EMBODIMENT 5

Alcohol dehydrogenase (ADH) was used as the enzyme, the NAD as the coenzyme, silica glass powders of approximately 0.05 μm in grain diameter as the carrier and the graphite as the electron collector. First, silica glass surfaces are chemically modified through the procedure as shown in the following equation.

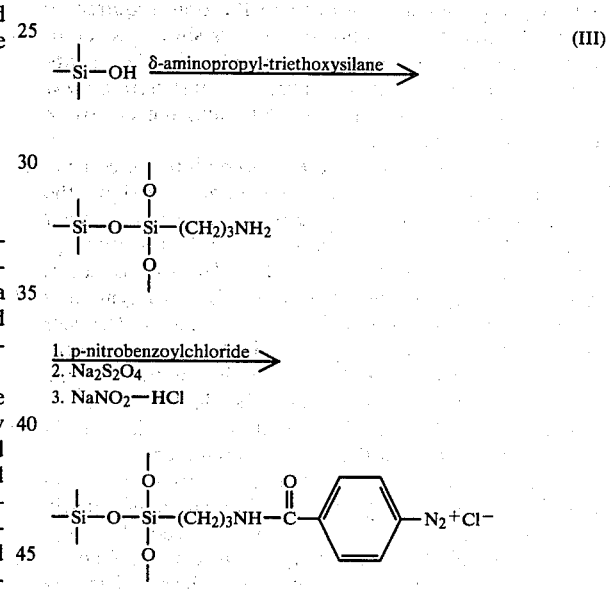

Figure 12:
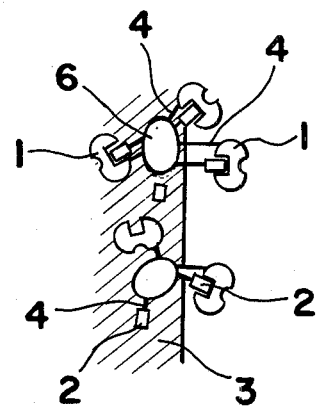

The NAD alone is, or NAD and ADH are simultaneously, diazo-coupled with the silica glass derivative (III), whereby the silica glass immobilizes the coenzyme alone or the coenzyme and enzyme. The above-described two types of glass powders are mixed with the graphite powders and are press-molded, respectively, whereby the coenzyme and coenzyme-enzyme immobilized electrode are made. FIG. 12 shows the typical construction scheme of the electrode by the use of glass powders 6.

The similar measurement as in the embodiment 1 by the use of the NAD immobilized electrode indicated that the linear relationship was obtained between the current values in the range of 0.5 to 3 U/ml in ADH.

Also, according to the similar measurement as in the embodiment 1 by the use of the NAD-ADH immobilized electrode, the current increase of 5 μA with respect to ethanol of $1\times 10^{-3}$ mol per l was recognized and the current reached the steady state value after 0.5 minute. And the estimation of the ethanol in the concentration range of $1 \times 10^{-4}$ to $2 \times 10^{-3}$ mol per l could be made.

According to the present invention, the activity of the enzyme can be measured by the use of the electrode with the coenzyme alone being immobilized, without combination with the immobilized enzyme. This operation is impossible to be made by the conventional system where the coenzyme is retained by the use of the semipermeable membrane.

Figure 1:
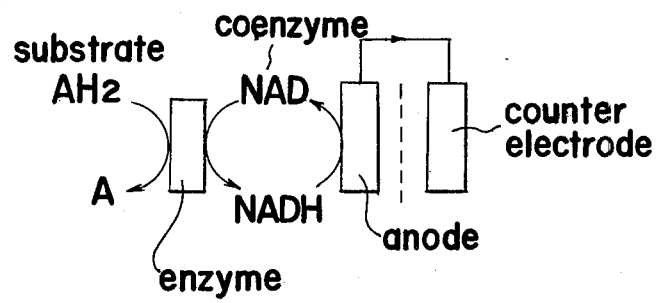
FIG. 1 is a typical view showing the relationship between enzyme reaction and electrode reaction.

Namely, even if the coenzyme is retained in the semipermeable membrane, the enzyme itself is macromolecular. Thus, the enzyme cannot diffuse into the membrane and cannot make a complex with the coenzyme, with the result that the reaction shown in FIG. 1 does not occur. In the conventional electrode, it is indispensable to use the semipermeable membrane to immobilize the coenzyme. On the contrary, in the present invention, the semipermeable membrane is not required for the immobilization of the coenzyme. Since the enzyme in the solution can form a complex with the coenzyme, the activity of the enzyme can be measured.

In addition, according to the coenzyme-enzyme immobilized electrode of the present invention, the current value provided is larger and the time required to reach the steady state current value is shorter as compared with the conventional electrode. This fact is apparent through comparison in typical construction view between the conventional electrode and the electrode of the present invention.

Figure 2:
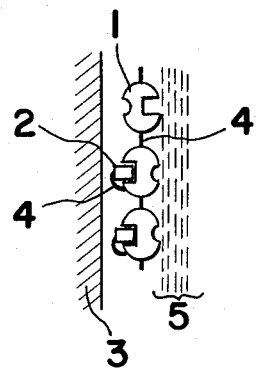
FIG. 2 and FIG. 3 are the typical views each showing the construction of the conventional enzyme-coenzyme immobilized electrode as referred to above.
Figure 3:
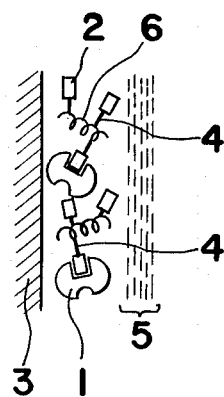

Namely, according to the conventional electrode shown in FIG. 2, the coenzyme immobilized on the semipermeable membrane is only brought into contact against the electron collector physically through approaching of the membrane to the electron collector. The probability of contact between the coenzyme and the electron collector is considerably small. In the case of FIG. 3, the coenzyme is combined with the macromolecular carrier, and the probability of the enzyme itself coming into contact against the electron collector is small due to the steric hindrance between the macromolecular carrier and the electron collector.

In the electrode of the present invention shown in FIGS. 4, 10, 11 and 12, the oxidation can be efficiently made, since the covalent bond 4 always keeps the coenzyme in electrical contact with the electron collector, even in the case where the coenzyme is immobilized on a carrier of a material different from the electron collector.

In the conventional embodiment, it is considered that the sufficient response current value and response time could not be provided due to not only the reducing effect in the contact probability between the coenzyme and the electron collector, but also the resisting effect with respect to diffusion of the substrate through the semipermeable membrane.

In the foregoing embodiments of the present invention, conductive materials such as carbon and $SnO_2$ were provided as examples of the electron collector. In addition, metal oxides such as $RuO_2$, $In_2O_3$ and $WO_3$ can be used as the electron collector in the present invention. NAD and NADP can be immobilized on the chemically modified surface of these electron collectors. Also, although albumin and glass were provided as examples of the carrier, high molecular organic compounds such as agarose and cellulose, and inorganic compounds such as alumina, silica alumina and zeolite, can be used. If there are no functional groups on the surface of these carriers, they can be used after addition of a functional group which allows covalent bonding to be achieved through chemical modification to immobilize the coenzyme.

While the present invention has been disclosed in terms of specific embodiments thereof, it is not intended that it be limited thereto, but rather only to the extent set forth hereinafter in the claims which follow.

What is claimed is:

1. A process for preparing a coenzyme immobilized electrode, which comprises (1) providing a coenzyme of oxidoreductase, said coenzyme being selected from the group consisting of NAD and NADP, (2) chemically modifying an electron collector, and (3) immobilizing said coenzyme on said electron collector through covalent bonding, so as to perform electron transfer with said electron collector.

2. A coenzyme immobilized electrode comprising at least a coenzyme of oxidoreductase and an electron collector, said coenzyme, which is selected from the group consisting of NAD and NADP, being immobilized through covalent bonding on said electron collector, said immobilized coenzyme being in electrical contact with said electron collector.

3. A coenzyme immobilized electrode in accordance with claim 2, wherein said coenzyme is immobilized on a chemically modified surface of said electron collector.

4. A coenzyme immobilized electrode in accordance with claim 2 or 3, wherein said electron collector is selected from the group consisting of carbon and a conductive metal oxide.

5. A coenzyme immobilized electrode in accordance with claim 4, wherein said conductive metal oxide is selected from the group consisting of $SnO_2$, $RuO_2$, $In_2O_3$ and $WO_3$.

* * * * *